United States Patent
Znaty et al.

(10) Patent No.: US 10,690,652 B2
(45) Date of Patent: Jun. 23, 2020

(54) METHOD FOR DETECTING SICKLE-CELL DISEASE AND KIT FOR IMPLEMENTING SAME

(71) Applicant: SCREENCELL, Sarcelles (FR)

(72) Inventors: David Znaty, Paris (FR); François Forestier, Paris (FR); Georges Uzan, Vitry sur Seine (FR); Cécile Aucant, Boussieres (FR)

(73) Assignee: SCREENCELL, Sarcelles (FR)

( * ) Notice: Subject to any disclaimer, the term of this patent is extended or adjusted under 35 U.S.C. 154(b) by 476 days.

(21) Appl. No.: 15/500,890

(22) PCT Filed: Aug. 4, 2015

(86) PCT No.: PCT/FR2015/052148
§ 371 (c)(1),
(2) Date: Jan. 31, 2017

(87) PCT Pub. No.: WO2016/020616
PCT Pub. Date: Feb. 11, 2016

(65) Prior Publication Data
US 2017/0219559 A1 Aug. 3, 2017

(30) Foreign Application Priority Data

Aug. 5, 2014 (FR) ..................... 14 57609
Dec. 18, 2014 (FR) ..................... 14 62701

(51) Int. Cl.
| | |
|---|---|
| *G01N 33/49* | (2006.01) |
| *G01N 33/80* | (2006.01) |
| *G01N 33/68* | (2006.01) |
| *G01N 1/40* | (2006.01) |
| *G01N 35/00* | (2006.01) |

(52) U.S. Cl.
CPC .......... *G01N 33/49* (2013.01); *G01N 1/4077* (2013.01); *G01N 33/491* (2013.01); *G01N 33/6893* (2013.01); *G01N 33/80* (2013.01); *G01N 35/00* (2013.01); *G01N 2001/4088* (2013.01); *G01N 2800/224* (2013.01)

(58) Field of Classification Search
CPC ..... G01N 33/49; G01N 1/4077; G01N 33/491
See application file for complete search history.

(56) References Cited

U.S. PATENT DOCUMENTS

2012/0077218 A1 3/2012 Randolph

FOREIGN PATENT DOCUMENTS

| FR | 2926090 A1 | 7/2009 |
|---|---|---|
| FR | 2952069 A1 | 5/2011 |
| WO | 2006/026735 A2 | 3/2006 |

OTHER PUBLICATIONS

Chikezie et al., Sodium metabisulfite-induced polymerization of sickle cell hemoglobin incubated in the extracts of three medicinal plants (*Anacardium occidentale, Psidium guajava*, and *Terminalia catappa*), Pharmacognosy Magazine, vol. 26, p. 126-132. (Year: 2011).*
Benjamin et al., "Cetiedil: Its Potential Usefulness in Sickle Cell Disease," Blood, Feb. 1, 1980, pp. 265-270, vo. 55, No. 2.
Hicks et al., "H b-type Total Percent Comparison of Results for Three Methods of Hemoglobin S Identification Analytical Methods Table 2. Sensitivity and Specificity of Various Screening Procedures for Sickle Cell Dlseasea," Clin. Chem., Jan. 1, 1973, pp. 533-535, vol. 19, No. 5.

* cited by examiner

*Primary Examiner* — Taeyoon Kim
*Assistant Examiner* — Tiffany M Gough
(74) *Attorney, Agent, or Firm* — Im IP Law; Chai Im; C. Andrew Im

(57) ABSTRACT

A method for detecting sickle-cell disease in an individual. A blood sample from an individual is brought into contact with an agent for inducing the sickling of red blood cells suitable for placing the red blood cells in a hypoxic condition. The blood sample is filtered through a porous membrane of which the pore size is determined to retain the sickled red blood cells, and allow the non-sickled red blood cells to pass through. The possible presence of a residue on the membrane is detected, during and/or after the filtering step. The presence indicating that the individual is suffering from sickle-cell disease.

12 Claims, 2 Drawing Sheets

METHOD FOR DETECTING SICKLE-CELL DISEASE AND KIT FOR IMPLEMENTING SAME

RELATED APPLICATIONS

This application is a § 371 application from PCT/FR2015/052148 filed Aug. 4, 2015, which claims priority from French Patent Application No. 14 57609 filed Aug. 5, 2014 and French Patent Application No. 14 62701 filed Dec. 18, 2014, each of which is incorporated herein by reference in its entirety.

FIELD OF THE INVENTION

The present invention lies in the field of testing for sickle cell disease. More particularly, it relates to a method for such testing using a blood sample from an individual, and also, on the one hand, a kit and, on the other hand, an automated device, for implementing a method according to the invention, for testing for sickle cell disease.

BACKGROUND OF THE INVENTION

Sickle cell disease, also referred to as sickle cell anemia, is an autosomal recessive genetic disease caused by an abnormality of the hemoglobin contained in the red blood cells, more specifically a structural abnormality of the β-chain of hemoglobin, characterized by the mutation of an amino acid of this β-chain, from glutamic acid to valine.

Sickle cell disease constitutes the most significant hemoglobinopathy throughout the world. Close to 120 million individuals are indeed thought to be carriers of the sickle cell trait.

Sickle cell disease is found in certain regions of the Indian subcontinent, in South America and in the Mediterranean basin. Intertropical Africa, that is to say the area located between the $15^{th}$ parallel south and the $20^{th}$ parallel north, is the most affected, with a rate of approximately one case of sickle cell disease per 65 births. The most affected countries are the Democratic Republic of the Congo, Senegal, Benin, and Angola. Mention may be made of a correlation, in these zones, with resistance to malaria, which supports the hypothesis that sickle cell disease would result from a process of natural selection by resistance to malaria, due to the difficulty for the plasmodium to carry out its cycle in sickle cells.

In France, homozygous sickle cell disease represents one birth in 1200. It is the primary genetic risk in Ile de France. In the West Indies, the rate reaches 1 case in 260 births. Sickle cell disease also affects the afro-American population, which is easily explained by the historical origin of the birth of this community in the United States, namely the mass of deportation of Africans in the context of the triangular trade, the descendents of whom remain nowadays affected by sickle cell disease.

Sickle cell disease thus constitutes a real public health problem, all the more since healthy carriers, who show no clinical sign, may be unaware that they are capable of transmitting this disease to their offspring. The World Health Organization predicts that, in a few decades, the number of carriers of such a hemoglobin abnormality will reach a rate of 8% of the worldwide population.

At the current time, there are several tests for testing for or diagnosing sickle cell disease. These tests are in particular based on the particular properties of the abnormal hemoglobin, termed hemoglobin S. These properties are for example, in the deoxygenated state, a decrease in solubility and a change in shape, called sickling. Under hypoxic conditions, the hemoglobin of the red blood cells undergoes gelling, and polymerizes into fibers which deform the red blood cells by elongating it, thereby giving it the appearance of a sickle.

The abnormal sickle nature of the hemoglobin can thus be detected by an insolubility test, termed Itano test, or by a hypoxia-induced sickling test, such as Emmel's test. More specifically, Emmel's test, well known to those skilled in the art, consists in bringing a blood sample into contact with a reducing agent, so as to trigger the phenomenon of sickling of the sickle red blood cells, and in observing under a microscope the effect of this agent on the shape of the red blood cells. However, these tests require specific laboratory equipment. In addition, they are not automatable.

Other identification tests currently used are based on electrophoresis techniques, high performance liquid chromatography (HPLC) techniques or molecular biology techniques, in particular techniques for detecting the disappearance of a restriction site in the nucleotide sequence of hemoglobin, or polymerase chain reaction (PCR) techniques. In addition to the fact that these tests require specific and expensive equipment, and also operator expertise, they are lengthy to carry out.

OBJECT AND SUMMARY OF THE INVENTION

The present invention aims to overcome the drawbacks of the methods for detecting the sickle nature of an individual that are proposed by the prior art, in particular those set out above, by providing a method of testing for sickle cell disease using a blood sample from an individual, which makes it possible to obtain a reliable result while at the same time being easy and rapid to carry out. The invention also aims at reducing the costs associated with carrying out this method.

An additional objective of the invention is that this method can be carried out either, on the one hand, without requiring specific and complex equipment or extensive operator expertise, or, on the other hand, by means of an automated device.

To this effect, the present invention advantageously takes advantage of a particular property of hemoglobin S produced by the individual with sickle cell disease, namely the property of polymerizing, under hypoxic conditions, inside the red blood cell. As explained above, under hypoxic conditions, formation of intracellular polymers causes a modification of the hemoglobin cytoskeleton, responsible for the sickling phenomenon, and also for the dehydration and stiffening of the erythrocytes. These erythrocyte deformability modifications contribute to the vaso-occlusive crisis, which is the main complication of the disease.

It has been discovered by the present inventors that, although normal red blood cells are capable of deforming, and of easily passing through pores having a size much smaller than their diameter, in particular smaller than this diameter by a few microns, on the other hand sickle red blood cells having undergone the sickling phenomenon, because of their particular sickle shape and their particular stiffness characteristic, are not, or are not very, deformable, and are incapable of passing through pores of the same size. Thus, it has been discovered by the present inventors that the difference in deformability of sickle red blood cells, compared with normal red blood cells, makes possible the differentiation of blood samples from sickle cell patients compared with blood cells from normal patients, by filtering such samples through a membrane of appropriate pore size.

The present invention thus provides a method of testing for sickle cell disease in an individual, which comprises the following successive steps, it being possible for steps a) and b) to be carried out successively or simultaneous:

a) bringing a blood sample, from an individual who is intended to be tested to determine whether or not he is suffering from sickle cell disease, into contact with an agent for inducing the sickling of sickle red blood cells, that is to say an agent capable of placing the red blood cells contained in the blood sample under hypoxic conditions, so as to cause sickling of the sickle red blood cells, b) filtering the blood sample, containing red blood cells, in particular possibly red blood cells having undergone the sickling phenomenon, through a porous membrane of which the pore size is determined such that said membrane is capable of retaining the red blood cells having undergone sickling, and of allowing the red blood cells which have not undergone sickling to pass through, and c) detecting, during and/or at the end of the filtering step b), the possible presence of a residue on the membrane, such a presence being associated with the fact that the individual has a sickle cell disease characteristic.

Such a possible residue presents itself in the form of a jelly, made up of aggregates of red-colored, sickle-shaped red blood cells.

In the present description, the expression "a sickle cell disease characteristic" is intended to mean the fact that the individual is of the homozygous SS type, that is to say suffering from the disease, or of the heterozygous AS type, that is to say carrying the disease.

The method according to the invention is simple and rapid to carry out. It makes it possible in particular to test for sickle cell disease in a few minutes, and what is more at low cost. The only consumables required for carrying it out are the agent for inducing sickling and the membrane. Its reliability has in addition been widely verified by the present inventors, this being for a large number of individuals, both healthy individuals and individuals suffering from sickle cell disease, by comparison with the results of biological tests of the prior art carried out for the same individuals.

The method according to the invention is carried out using a total blood sample, so that it does not require complex equipment for prior treatment of the blood sample. Depending on the conditions for carrying out the method, the only pretreatment that this sample may have to undergo is bringing it into contact with an anticoagulant at the time it is taken from the individual, for example into contact with ethylenediaminetetraacetic acid (EDTA), in a manner which is conventional in itself for blood samples for biological tests.

In particular, the method according to the invention comprises no step of bringing the blood sample into contact with a cell lysis agent, such as saponin. It is indeed a blood sample containing red blood cells which is subjected to the filtering step b), and not a solution containing hemoglobin, which could be obtained from the blood sample by means of a cell lysis step.

According to the present invention, this blood sample containing red blood cells can be subjected to the filtering step simultaneously with the step of bringing into contact with the agent for inducing sickling of the sickle red blood cells. When, on the contrary, the blood sample is subjected to the filtering step b) after step a) of bringing into contact with the agent for inducing sickling of the sickle red blood cells, this step b) is preferentially carried out directly after step a), that is to say that after the step a) of bringing into contact with the agent for inducing sickling has been carried out, and the blood sample, which still contains red blood cells, is directly subjected to the filtering step b), without undergoing any intermediate step of treatment, centrifugation, separation of certain components, etc.

The method according to the invention is applicable both in adults and in newborns, for early diagnosis of the disease, using a blood sample taken from the umbilical cord. In particular, even in newborns, the difference in appearance of the membrane at the end of the filtering step, between a sickle cell blood sample and a normal blood sample, is advantageously visible to the naked eye, despite the small amount of sickle red blood cells present in umbilical blood, including for samples of this blood of small volume. The method according to the invention can as a result be advantageously part of a more global, noninvasive process for newborns.

An additional advantage of the method according to the invention is the possibility of archiving the membrane obtained after the filtering step, and on which a residue made up of sickle red blood cells has been detected, with a view to the subsequent implementation of biological tests using these sickle red blood cells located on the membrane, or blocked in the pores of the latter. For example, the DNA of these red blood cells may then be extracted, for analysis of this DNA by molecular biology techniques. This in particular proves to be particularly advantageous when the testing method according to the invention is carried out in developing countries, which are not very well equipped with genetic analysis equipment. After the filtering step, the membranes obtained for the patients for whom the method according to the invention has made it possible to establish a status "suffering from the disease" can be easily conveyed to reference laboratories located remotely from the site of the test, for carrying out additional examinations.

The archiving of the membranes at the end of the method according to the invention also makes it possible to ensure traceability of the results.

The agent for inducing sickling of the sickle red blood cells, capable of placing the red blood cells contained in the blood sample with which it is brought into contact under hypoxic conditions, may be of any type that is conventional in itself. It is within the competence of those skilled in the art to identify the agents which correspond to such a characteristic, on the basis of their general knowledge and/or experimentally. To this effect, those skilled in the art will be able to evaluate, for a blood sample brought into contact with a candidate agent for inducing sickling, the oxygen partial pressure or the oxygen saturation, a low oxygen partial pressure and a decreased oxygen saturation being gasometric controls of hypoxia. More specifically, an oxygen partial pressure less than or equal to 20 mmHg or an oxygen saturation of between 30% and 60% is representative of an hypoxia capable of inducing sickling in a sickle cell individual.

It is also within the competence of those skilled in the art to determine the pore size of the porous membrane which makes it possible to retain the red blood cells that have undergone sickling and to allow the red blood cells which have not undergone sickling to pass through. To this effect, those skilled in the art will be able in particular to rely on the fact that a normal red blood cell has a diameter of approximately 8 µm, and that its deformability allows it to pass through capillaries of 2 to 3 µm, whereas sickle red blood cells are incapable of doing this. The determination of the size of appropriate pores may for example be determined empirically by those skilled in the art, using a blood sample from an individual who is healthy in terms of sickle cell disease and a blood sample from an individual suffering from sickle cell disease, by placing these blood samples under hypoxic conditions, in particular according to Emmel's method, which is conventional in itself, and carrying out a test of filtering on a membrane of given pore size, in order to verify whether or not this pore size complies with the present invention, that is to say allows normal red blood cells to pass through, while prohibiting sickle red blood cells from doing so.

In particular embodiments, the method according to the invention also corresponds to the following characteristics, implemented separately or in each of their technically operative combinations.

The agent for inducing sickling of sickle red blood cells is preferably a reducing agent which, by consuming the oxygen in the medium, such that the hemoglobin present in this medium is under hypoxic conditions, causes the reaction of sickling of the sickle red blood cells.

In particular embodiments of the invention, the agent for inducing sickling of sickle red blood cells is a metabisulfate salt, for example sodium metabisulfate.

In variants of the invention, the bringing of the blood sample into contact with the agent for inducing sickling of sickle red blood cells is carried out by mixing the blood sample with a buffer solution having a pH of between 6.8 and 7.4, containing the agent for inducing sickling. This solution is in particular free of cell lysis agent, such as saponin.

This solution may contain between 1% and 10%, preferably between 2% and 5%, for example approximately 5%, by weight of the agent for inducing sickling, relative to the total volume of the solution.

Such a concentration range of the agent for inducing sickling in the solution advantageously makes it possible to cause sickling of the sickle red blood cells in a reduced time.

In particular embodiments of the invention, the bringing of the blood sample into contact with the agent for inducing sickling is carried out for a period of greater than or equal to 30 seconds, preferably greater than or equal to 1 minute, and preferentially of between 2 and 3 minutes. Such a period of incubation of the blood sample with the agent for inducing sickling of sickle red blood cells advantageously makes it possible to obtain a degree of sickling that is sufficient for the difference in appearance of the membrane at the end of the filtering step to be visually detectable with the naked eye.

In other variants of the invention, the membrane used for the filtering is pre-impregnated with the agent for inducing sickling, so that the bringing of the blood sample into contact with the agent for inducing sickling is carried out during the actual filtering of the blood sample through the membrane. The time required for carrying out the method according to the invention is thus accordingly shorter.

In other further variants of the invention, which are particularly advantageous in terms of feasibility and rapidity of implementation of the method, the bringing of the blood sample into contact with the agent for inducing sickling is carried out, prior to the filtering step b), by depositing the blood sample on a porous filter with a pore size that is determined so as to be capable of allowing red blood cells that have not undergone sickling and red blood cells that have undergone said sickling to pass through, and that is impregnated with the agent for inducing sickling. This filter is placed on the membrane. The expression "placed on" is intended to mean that the filter is located above the membrane, in the direction of flow of the blood sample, and preferably in contact with the membrane, so as to allow the blood sample to go through the filter up to the membrane by capillary action.

This filter may for example have a pore size of greater than 8 μm.

Such a filter may in particular be of the absorbent type, for example based on fibers, in particular on cotton fibers, such as the filtration papers sold under the brand name WHATMAN®.

This filter has been impregnated, prior to carrying out the method according to the invention or in a preliminary step thereof, with a solution containing the agent for inducing sickling, for example at a concentration of approximately 25% by weight, relative to the total volume of the solution. This impregnation can in particular be carried out by soaking the filter in the solution. It is preferentially followed by a step of drying the filter thus impregnated, for example in the open air and at ambient temperature, or with slight heating.

After drying, this filter advantageously retains a sufficient amount of agent for inducing sickling to induce the sickling of the sickle red blood cells contained in a blood sample which passes through it by capillary action, before coming into contact with the membrane placed under the filter.

The induction of the sickling then advantageously occurs in a very short time, of about a few seconds.

The method according to the invention can advantageously be carried out using a very small volume of blood, in particular of between 10 and 50 μl, preferably of between 15 and 25 μl, for example of between 12 and 18 μl or else approximately equal to 20 μl.

The membrane used for the filtering step may be of any type, the only condition being that the materials of which it is formed are inert with respect to the components of the blood sample. By way of example, the membrane used is made of polycarbonate.

In particular embodiments of the invention, the pore size of the membrane is between 2 and 8 μm, preferably between 3 and 6 μm or between 6 and 7 μm. Such a porosity advantageously allows the red blood cells from the blood of normal individuals, and also the leucocytes, to pass through the membrane, while at the same time preventing the sickle red blood cells having undergone the sickling phenomenon from passing through.

The membrane may have any degree of porosity.

The detection of the possible presence of a residue on the filtering membrane can be carried out by visual observation of the appearance of the surface of the membrane, in particular with the naked eye, or by optical detection means of the infrared ray, laser ray, etc., type.

In particular embodiments of the invention, the detection of the possible presence of a residue on the membrane is carried out by detection of a possible red coloration of the membrane, during and/or at the end of the filtering step.

Otherwise, the detection of the possible presence of a residue on the filtering membrane can be carried out by detection of an overthickness of the membrane, due to the clump of sickle red blood cells not having been able to pass through the pores of the membrane.

In addition, the sickle red blood cells having undergone sickling, by remaining on the membrane during filtration, lead to clogging of the membrane, by blocking of the pores of the latter, and as a result to a decrease in the filtration flow rate. This results in a filtering time that is longer than in the absence, in the sample, of sickle red blood cells. This difference in filtering time, for identical filtering conditions, is about a few tens of seconds, sufficient to make it possible to determine, for example in comparison with a control normal individual, whether or not the individual for whom testing is carried out is suffering from sickle cell disease.

In particular embodiments of the invention, the membrane is placed on a member made of absorbent material. This is intended to mean that a member made of absorbent material is located below the membrane, in the direction of flow of the blood sample, and preferably in contact with the membrane, so as to allow the blood sample to go through the membrane up to the member made of absorbent material by capillary action.

The detection of the possible presence of a residue on the membrane is carried out by detecting a possible change in coloration of this member made of absorbent material. The absence of such a change in coloration is representative of the presence of a residue on the membrane, and of an individual suffering from sickle cell disease. The occurrence of such a change in coloration, to the color red, is for its part representative of the absence of residue on the membrane, and of an individual who is healthy with respect to sickle cell disease.

This member made of absorbent material can for example be of the fiber-based type, such as the filtration papers sold under the brand name WHATMAN®.

Otherwise, in the advantageous configuration of the invention in which a filter impregnated with agent for inducing sickling is placed on the membrane, the detection of the possible presence of a residue on the membrane can be carried out by detecting a possible red coloration of this filter, at the end of the filtering step b). The occurrence of such a red coloration is then representative of the presence of a residue on the membrane, and of an individual suffering from sickle cell disease. The absence of such a red coloration is for its part representative of the absence of residue on the membrane, and of an individual who is healthy with respect to sickle cell disease.

In particularly advantageous embodiments of the invention, the membrane is inserted between the porous filter and the member made of absorbent material, preferably so as to be in contact with each of them, prior to carrying out step a) of bringing the blood sample into contact with the agent for inducing sickling.

The filtering step can be carried out either by suctioning, or by pushing, the blood sample through the membrane, using methods which are conventional in themselves to those skilled in the art. Otherwise, it can be carried out by transfer by capillary action, the filtering membrane then being for example superimposed on a member made of absorbent material. In such an embodiment in which the filtering membrane is superimposed on a member made of absorbent material, the filtering step b) can also be assisted by suctioning or pushing the blood sample through the membrane.

The pressure used for the filtering step is preferably constant. Its value can easily be determined by those skilled in the art, theoretically or empirically, according to the time desired for the filtering step, of the volume of sample to be filtered and of the characteristics of the membrane used, in particular its pore size and its degree of porosity. Preferentially, the above conditions of the method according to the invention are chosen so as to obtain a short filtering time, for example of approximately two minutes, or less.

The method according to the invention can be carried out using a few microliters to a few milliliters of blood. It can in particular advantageously be carried out using approximately 10 µl of blood, which corresponds substantially to the volume of a drop of blood taken from a finger.

The present invention also relates to means for implementing a method according to the invention. Such implementing means may be of various types, each especially being particularly suitable for the configuration of a type of territory on which the method according to the invention is liable to be carried out.

Thus, according to one of its aspects, the present invention relates to a kit for testing for sickle cell disease in an individual. This kit comprises an agent for inducing sickling of sickle red blood cells, capable of placing the red blood cells contained in a blood sample in a hypoxic condition, and a porous membrane of which the pore size is determined in order to be capable of retaining red blood cells having undergone said sickling, and of allowing red blood cells which have not undergone sickling to pass through. This kit is free of cell lysis agent.

The agent for inducing sickling and the membrane can correspond to one or more of the characteristics stated above with reference to the testing method according to the invention.

The inducing agent may be impregnated on the membrane.

In variants of the invention, the kit comprises a buffer solution having a pH of between 6.8 and 7.4, containing the agent for inducing sickling, and free of cell lysis agent. This solution may in particular correspond to one or more of the characteristics described above.

For example, the kit according to the invention may comprise a buffer solution having a pH of between 6.8 and 7.4, containing sodium metabisulfite at 5% by weight by volume, and a membrane having a pore size of 3.5 µm, of 4.5 µm or of 6.5 µm.

In different embodiments of the invention, the kit comprises a porous filter of which the pore size is determined in order to be capable of allowing red blood cells which have not undergone sickling and red blood cells having undergone sickling to pass through, and which is impregnated with the agent for inducing sickling.

The kit according to the invention may also comprise a member made of absorbent material, which is preferably capable of being superimposed with the membrane, in contact with the latter.

This filter and this member made of absorbent material may each correspond to one or more of the characteristics described above concerning them with reference to the method of testing for sickle cell disease according to the invention. They may be made of the same material, or of different materials.

The membrane, the filter and the member made of absorbent material may be present in the kit separate from one another. Otherwise, they may be present therein in the form of a stratified assembly of which they form the constituent layers which are preferably pressed firmly together, the membrane being inserted between the filter and the member made of absorbent material. This assembly can be maintained in a solid support.

In particular embodiments of the invention, the kit also comprises a filtering module, for example of the type comprising, assembled or able to be assembled with one another:
  a reservoir for the sample to be filtered,
  a membrane receptacle, in which the filtering membrane may already be positioned, or may be intended to be placed,
  and an end piece comprising an orifice for discharging the filtrate, and also preferably for applying a reduced pressure causing suctioning of the mixture contained in the reservoir through the membrane.

This filtering module may also comprise means for suctioning the liquid contained in the reservoir through the membrane, in particular a tube with a reduced internal pressure, such as a VACUTAINER® tube.

The kit according to the invention may also comprise a receptacle for collecting a blood sample from an individual, such as a tube with a reduced internal pressure equipped with a stopper comprising a closure member which can be pierced, of VACUTAINER® type, containing, where appropriate, an anticoagulant, for example EDTA.

The kit may also comprise instructions of use for carrying out a method according to the invention.

Preferentially, all of the constituents of the kit according to the invention are of disposable type.

Such a kit, which is easily transportable, is particularly suitable for use in developing countries, for example in African regions, which have little medical analysis infrastructure.

According to another of its aspects, the present invention relates to a device for carrying out a method according to the invention, which comprises:
- automated means for bringing the blood sample from the individual into contact with the agent for inducing sickling of sickle red blood cells,
- automated means for filtering, through the membrane, the blood sample containing red blood cells directly after the step of bringing the blood sample into contact with the agent for inducing sickling of sickle red blood cells, that is to say without any intermediate step other than a moving step, in particular without any intermediate step of treatment, centrifugation, separation of constituents, etc. These automated filtering means may be the same as the automated means for bringing the blood sample into contact with the agent for inducing sickling, and
- means for optical detection of the possible presence of a residue on the membrane, during or at the end of the filtering step, for example means for reading the membrane, of the type by laser ray.

This device may also comprise an automated module for conveying a receptacle containing the blood sample from one of the automated modules above to another, for example such as a module commonly denoted by the expression "sample changer", and also a module for automatically controlling one or more of the various modules above for carrying out one or more of the steps of a method of testing for sickle cell disease according to the invention.

Such an automated device is particularly suitable for use in "industrialized" countries, equipped with sophisticated analysis laboratories, for high-throughput testing.

BRIEF DESCRIPTION OF THE DRAWINGS

The characteristics and advantages of the invention will emerge more clearly on reading the examples hereinafter, given simply by way of illustration and which are in no way limiting of the invention, with the support of FIGS. 1 to 4, in which.

DETAILED DESCRIPTION OF THE EMBODIMENTS

Figure 1:
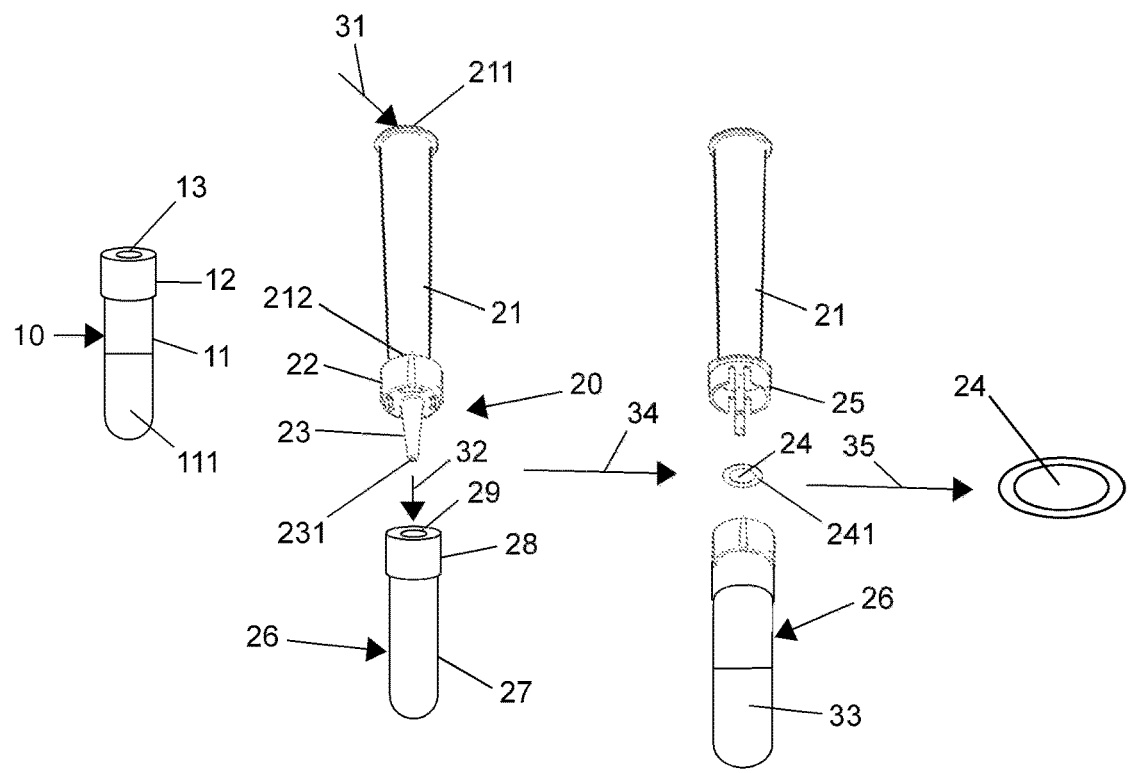
FIG. 1 represents diagrammatically the constituents of a kit for testing for sickle cell disease in accordance with the present invention, and illustrates the various steps of a method of testing for sickle cell disease in accordance with the present invention, carried out by means of this kit.

A kit for testing for sickle cell disease according to the invention is represented diagrammatically in FIG. 1. The relative dimensions of the various constituents of this kit are not representative of reality.

This kit comprises a first tube 10, termed sampling tube, comprising a body 11 and a stopper 12 comprising a closure member 13 which can be pierced with a needle, known as a septum. An anticoagulant, in particular EDTA, is contained in the body 11 of the tube 10.

The kit also comprises a filtering module 20. This filtering module can in particular be as described in patent documents FR 2952069A or FR 2926090A in the name of the present applicant.

Diagrammatically, the filtering module 20 comprises the following elements. For reasons of clarity, some of these elements are represented in FIG. 1 separated from one another, whereas they are in reality initially assembled together.

The filtering module 20 thus comprises a reservoir 21 for receiving the sample to be filtered, comprising, at a first end 211, an opening for feeding with sample.

At a second end 212, in particular opposite said first end 211, the reservoir 21 is secured to a member 25 for receiving a filtering membrane 24. This filtering membrane 24 is mounted for this purpose in a rigid membrane support 241.

The membrane 24 is for example made of polycarbonate. It has for example a random pore distribution, a pore diameter of 3.5 µm, and a pore density of 100 000 pores/cm$^2$.

The filtering module also comprises a hollow end piece 22, reversibly attached around the member 25 for receiving the membrane, and comprising a support 23 for a tip for piercing a septum, pierced with a channel 231 which opens out at its end, for discharging the filtrate and applying the suction.

The filtering module also comprises a tube 26 with a reduced internal pressure, of VACUTAINER® type, termed collecting tube, comprising a body 27 and a stopper 28 with a septum 29. The internal pressure in the collecting tube 26 is for example initially between 76 and 200 mmHg.

The kit also comprises a buffer solution at pH 7.2, termed reducing solution, containing, for 1 liter of solution, 8.41 g of phosphate buffered saline (PBS), 1.8 g of EDTA and distilled water in a sufficient amount to obtain a total volume of 1000 ml. The pH thereof is adjusted to the desired value with sodium hydroxide (NaOH). The reducing agent, sodium metabisulfate, is added to this solution at a concentration of 5% w/v.

A method according to one particular embodiment of the invention is carried out in the following way, by means of this kit.

For an individual to be tested, a blood sample is taken and collected in the sampling tube 10, according to the standard protocol for taking a blood sample dedicated to the instructions for a complete blood count (CBC). Schematically, after having placed a tourniquet on the arm, the radial or cubital vein is punctured using a vacuum device, for example by means of a beveled needle connected to the sampling tube 10. A volume of blood 111, for example 5 ml, is collected in the sampling tube 10, and immediately brought into contact with EDTA.

The blood samples are preferably used within 24 h after they have been taken.

The desired volume of the blood sample is then taken from the sampling tube 10, and diluted in the reducing solution, so as to achieve the desired total volume. The sickle red blood cells possibly contained in the blood sample then undergo the sickling phenomenon.

After 1 to 2 min, the final solution thus obtained is placed in the reservoir 21 of the filtering module 20, as indicated at 31 in FIG. 1. The tip attached to the tip support 23 of the end piece 22 is then inserted through the septum 29 of the collecting tube 26, as indicated at 32 in FIG. 1.

Owing to the reduced pressure in the collecting tube 26, the content of the reservoir 21 is suctioned through the membrane 24. The filtrate 33 passing through this membrane 24 and collected in the collecting tube 26 comprises the blood containing the normal red blood cells and the leucocytes. The sickle red blood cells which are rigid and sickle-shaped are for their part retained by the membrane 24.

At the end of the filtration, the filtering module 20 is disassembled, as indicated at 34 in FIG. 1, so as to collect the membrane 24, as indicated at 35.

This membrane 24 is observed visually, so as to detect thereon any possible red coloration and/or to detect the possible presence of an overthickness on its surface. Such a possible coloration and/or such a possible overthickness are indicative of an individual suffering from sickle cell disease.

Such a method according to the invention was carried out in the following way, for 16 patients suffering from sickle cell disease and for 16 normal patients.

The biological diagnosis of sickle cell disease had been established beforehand either by electrophoresis in the presence of ampholines (diagnosis referred to as focusing of the hemoglobin), or by HPLC.

Volumes respectively of 100, 50 and 10 µl of blood from each of the individuals were diluted in the reducing solution, so as to achieve a total volume of 8.6 ml.

For each individual and each dilution, the diluted sample thus obtained was placed in the reservoir 21 of a filtering module 20, and subjected to filtration through the membrane 24.

The filtration time was between 1 and 2 min.

At the end of the filtering step, each membrane was recovered and visually observed.

Figure 2:
FIG. 2 shows a photograph of the membranes obtained after carrying out a method according to the invention, using a blood sample, (A) from a normal individual, (B) from a sickle cell individual, for dilution rates of the blood sample in a solution containing an agent for inducing sickling respectively of 100, 50 and 10 µl of blood sample in a total volume of 8.6 ml of this solution.

For the three dilution levels, an example of the membranes obtained for a normal individual (A) and for a sickle cell individual (B) are shown in FIG. 2. These results are representative of each category of individuals tested.

A coloration of the membranes from the sickle cell individual is clearly observed, this being for all the initial volumes of blood sample, including for the volume of 10 µl. This coloration is dark red in reality. No coloration is observed for the membranes from the healthy individual.

Figure 3:
FIG. 3 shows images obtained by observation under a microscope, with a magnification of 200 times, of the membranes of FIG. 2, corresponding to the volume of 10 µl of blood sample, (A) for the normal individual, (B) for the sickle cell individual.

An observation under the microscope of the membranes obtained for an initial volume of blood sample of 10 µl was carried out. The images obtained are shown in FIG. 3. It is observed therein that the membrane used to filter the normal blood sample comprises no red blood cell on its surface, whereas the membrane used to filter the sickle blood sample comprises red blood cell aggregates on its surface.

These results are representative of all the results obtained, for each of the two categories of individuals tested. For all of the samples taken, a deposit of red blood cells was observed at the surface of the membranes when the blood came from affected patients. This deposit was never observed when the blood came from healthy individuals. The sickling induced by sodium metabisulfite thus made the sickle red blood cells rigid and undeformable, incapable of penetrating, by deformability, through the pores of the membrane, as the red blood cells from the normal individuals did.

This clearly demonstrates the reliability of the method in accordance with the invention for testing for sickle cell disease. Even using a blood sample with a volume of 10 µl, this method makes it possible to distinguish between individuals suffering from the disease and healthy individuals.

Figure 4:
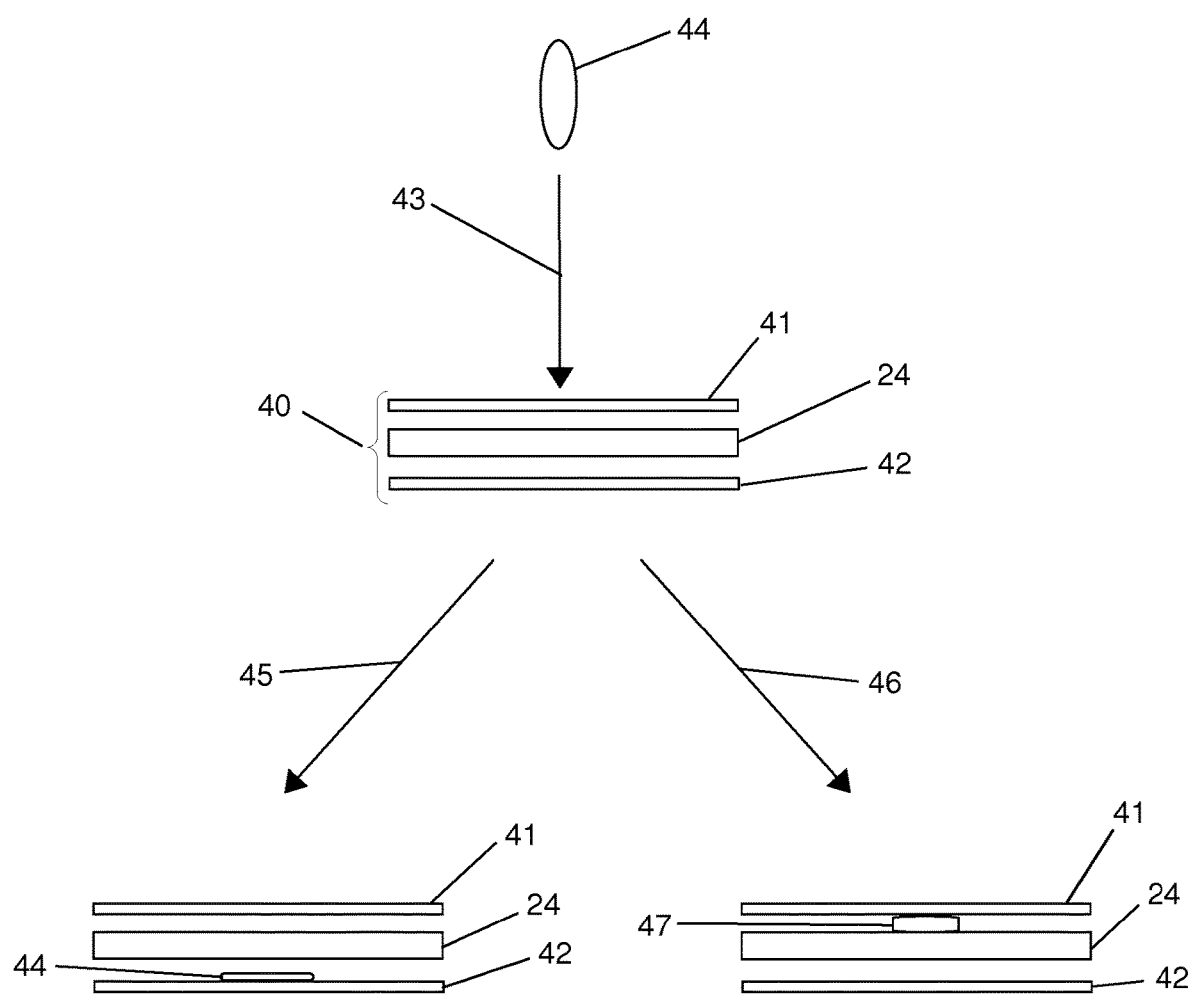
FIG. 4 illustrates diagrammatically the steps of a method of testing for sickle cell disease according to a variant of the invention.

FIG. 4 illustrates a particularly advantageous embodiment of the invention, using a kit in accordance with the invention, comprising a stratified filtering assembly 40 comprising the following successive constituent layers: a porous filter 41, a membrane 24 and a member made of absorbent material 42. In this figure, these various layers are represented spaced out from one another for reasons of clarity. They are in reality in contact with one another. Moreover, the relative thicknesses of these various layers are not in any way representative of reality.

The membrane 24 corresponds to the characteristics described above.

The filter 41 and the member made of absorbent material 42 can be made of the same material, or of different materials.

The filter 41 has a pore size that is sufficient to allow red blood cells which have not undergone sickling and red blood cells having undergone sickling to pass through.

For example, the filter 41 and the member made of absorbent material 42 are both WHATMAN® No. 40 filtration papers, based on cotton fibers, having a thickness of 22 µm, a grammage of 95 g/m$^2$ and a retention of 8 µm.

This filter 41 and this member made of absorbent material 42 are for example in the form of disks, in particular having a diameter of between 8 mm and 2 cm, for example of approximately 9 mm.

The filter 41 was pre-impregnated by soaking in a solution containing the agent for inducing sickling, for example sodium metabisulfite, at a concentration of 25% w/v, then dried.

A method of testing for sickle cell disease can be carried out in the following way, by means of such a filtering assembly 40.

In a first step, illustrated at 43 in FIG. 4, a blood sample 44 is deposited on the upper surface of the filter 41. The volume of this blood sample 44 is for example approximately 15 µl, that is to say approximately the equivalent of a drop of blood.

This sample passes through the filter 41, by capillary action. During this phase, it is in contact with the agent for inducing sickling. Upon this contact, the sickle red blood cells possibly contained in the blood sample 44 undergo the sickling phenomenon.

Depending on whether the blood sample comes from an individual suffering from sickle cell disease or from an individual who is healthy with respect to this disease, the following events then occur.

If the individual is healthy with respect to sickle cell disease, as indicated at 45 in FIG. 4, the blood sample 44, which does not contain red blood cells having undergone sickling, passes through the membrane 24, still by capillary action, and is absorbed by the member made of absorbent material 42. The latter changes color, to a red color. The filter 41 for its part retains its initial coloration. The testing for an absence of sickle cell disease characteristic is thus carried out by observation of the filter 41 and/or of the member made of absorbent material 42, the first having kept its initial coloration and the second having become red in color.

If the individual is suffering from sickle cell disease, as indicated at 46 in FIG. 4, the red blood cells 47, contained in the blood sample 44 and having undergone sickling, are blocked by the membrane 24. Observation of the member made of absorbent material 42 after a few seconds shows that the latter has kept its initial coloration, since the red blood cells never came as far as said member. The filter 41, for its part, is still in contact with the sickle-shaped red blood cells 47, some of which, contrary to what is represented in FIG. 4, still remain trapped in its pores. It consequently has a red coloration. Thus, the testing for having a sickle cell disease characteristic is also carried out by observation of the filter 41 and/or of the member made of absorbent material 42, the first having becoming red in color and the second having kept its initial coloration.

This testing was advantageously very simple and rapid to carry out, and what is more using a very small volume of blood.

The invention claimed is:

1. A method of testing for sickle cell disease in an individual, comprising the following successive steps, steps a) and b) being carried out successively or simultaneously:
   a) bringing a blood sample from the individual into contact with an agent for inducing sickling of sickle red blood cells placing red blood cells contained in the blood sample in a hypoxic condition, wherein the agent for inducing sickling is metabisulfite salt, and mixing said blood sample with a buffer solution having a pH of between 6.8 and 7.4, containing the agent for inducing sickling and free of a cell lysis agent;
   b) filtering said blood sample containing the red blood cells through a porous membrane having a pore size that retains the red blood cells which have undergone said sickling, and allows the red blood cells which have not undergone said sickling to pass through; and
   c) detecting a presence of a residue on the porous membrane, during or at an end of the filtering step, wherein the presence of the residue indicates that the individual has a sickle cell disease.

2. The method as claimed in claim 1, wherein a porosity of the membrane is between 2 and 8 µm.

3. The method as claimed in claim 2, wherein the porosity of the membrane is between 3 and 6 µm.

4. The method of claim 2, wherein the porosity of the membrane is between 6 and 7 µm.

5. The method as claimed in claim 1, wherein the buffer solution contains between 1% and 10% by weight of the agent for inducing sickling, relative to a volume of the buffer solution.

6. The method as claimed in claim 1, wherein the buffer solution contains between 2% and 5% by weight of the agent for inducing sickling, relative to the volume of the buffer solution.

7. The method as claimed in claim 1, wherein the bringing step is carried out for a period of greater than or equal to 30 seconds.

8. The method as claimed in claim 7, wherein the bringing step is carried out for a period of greater than or equal to 1 minute.

9. The method as claimed in claim 1, wherein the bringing step is carried out, prior to the filtering step, by depositing said blood sample on a porous filter with a pore size that allows the red blood cells which have not undergone sickling and the red blood cells which have undergone said sickling to pass through, the porous filter is impregnated with the agent for inducing sickling and the filter is placed on the porous membrane.

10. The method as claimed in claim 1, wherein a volume of said blood sample is between 10 and 50 µl.

11. The method as claimed in claim 1, wherein the detecting step comprises a step of detecting a red coloration of the porous membrane.

12. The method as claimed in claim 1, wherein the porous membrane is placed on a member made of absorbent material; and wherein the detecting step comprises a step of detecting a change in coloration of the member made of absorbent material, an absence of said change in coloration is representative of the presence of the residue on the porous membrane.

* * * * *